US011590828B2

(12) United States Patent
Garcia

(10) Patent No.: US 11,590,828 B2
(45) Date of Patent: *Feb. 28, 2023

(54) LATERAL VENT STICK AIR FRESHENER

(71) Applicant: Energizer Brands II, LLC, St. Louis, MO (US)

(72) Inventor: Raul Garcia, Draper, UT (US)

(73) Assignee: Energizer Group Limited, High Wycombe (GB)

( * ) Notice: Subject to any disclaimer, the term of this patent is extended or adjusted under 35 U.S.C. 154(b) by 69 days.

This patent is subject to a terminal disclaimer.

(21) Appl. No.: 17/121,122

(22) Filed: Dec. 14, 2020

(65) Prior Publication Data

US 2021/0094393 A1    Apr. 1, 2021

Related U.S. Application Data

(63) Continuation of application No. 17/082,285, filed on Oct. 28, 2020, which is a continuation of application No. 16/173,865, filed on Oct. 29, 2018, now Pat. No. 10,850,594, which is a continuation of application No. 15/255,537, filed on Sep. 2, 2016, now Pat. No. 10,232,683.

(60) Provisional application No. 62/247,544, filed on Oct. 28, 2015.

(51) Int. Cl.
| *B60H 3/00* | (2006.01) |
| *B60H 1/34* | (2006.01) |
| *A61L 9/12* | (2006.01) |
| *A61L 9/04* | (2006.01) |

(52) U.S. Cl.
CPC .......... *B60H 3/0007* (2013.01); *A61L 9/042* (2013.01); *A61L 9/12* (2013.01); *B60H 1/3421* (2013.01); *B60H 3/00* (2013.01); *B60H 3/0028* (2013.01); *A61L 2209/15* (2013.01); *B60H 2001/3471* (2013.01); *B60H 2003/0042* (2013.01)

(58) Field of Classification Search
CPC ...... B60H 3/0007; B60H 3/00; B60H 3/0028; B60H 2001/3471; B60H 2003/0042; A61L 9/042; A61L 9/12; A61L 2209/15; A61L 9/125
USPC ................................................ 239/53–57, 60
See application file for complete search history.

(56) References Cited

U.S. PATENT DOCUMENTS

| 4,903,584 A | 2/1990 | Styles |
| 5,762,549 A | 6/1998 | Scheuer et al. |
| D437,041 S | 1/2001 | Eisenbraun |
| D594,954 S | 6/2009 | Wheatley |
| 7,687,037 B2 | 3/2010 | Wheatley et al. |
| 7,687,038 B2 | 3/2010 | Wheatley et al. |

(Continued)

OTHER PUBLICATIONS

United States Patent and Trademark Office, Office Action for U.S. Appl. No. 15/255,537, filed Mar. 14, 2018, USA.

(Continued)

*Primary Examiner* — Christopher S Kim
(74) *Attorney, Agent, or Firm* — Lee & Hayes, P.C.

(57) ABSTRACT

An air freshener has a carrier with a pair of tabs defining a gap. A center tab extends from the pair of tabs and defines a longitudinal axis. At least one scented body is carried by one of the pair of tabs. The pair of tabs and the at least one scented body extend laterally with respect to the longitudinal axis of the center tab in opposite directions. The pair of tabs and the at least one scented body have a lateral width greater than a longitudinal depth.

20 Claims, 4 Drawing Sheets

(56) References Cited

U.S. PATENT DOCUMENTS

| | | | |
|---|---|---|---|
| D640,359 S | 6/2011 | Irvin | |
| D650,892 S | 12/2011 | Wheatley et al. | |
| 8,147,761 B2 | 4/2012 | Wheatley et al. | |
| D667,100 S | 9/2012 | Hakim | |
| 8,460,609 B1 | 6/2013 | Wheatley et al. | |
| 8,480,960 B2 | 7/2013 | Wheatley et al. | |
| D689,181 S | 9/2013 | Irvin | |
| 8,685,330 B2 | 4/2014 | Irvin et al. | |
| 9,155,812 B1 | 10/2015 | Bourne | |
| 9,314,543 B2 | 4/2016 | Bourne | |
| 10,232,683 B2 * | 3/2019 | Garcia | B60H 3/00 |
| 10,850,594 B2 * | 12/2020 | Garcia | B60H 3/0007 |
| 2011/0108632 A1 | 5/2011 | Brandenburg et al. | |
| 2014/0113538 A1 | 4/2014 | Irvin et al. | |
| 2021/0039479 A1 * | 2/2021 | Garcia | B60H 3/0007 |
| 2021/0094393 A1 | 4/2021 | Garcia | |

OTHER PUBLICATIONS

United States Patent and Trademark Office, Notice of Allowance for U.S. Appl. No. 15/255,537, filed Sep. 5, 2018, USA.
Office Action for U.S. Appl. No. 17/082,285, dated Jul. 22, 2022, Garcia, "Lateral Vent Stick Air Freshener", 8 pages.

* cited by examiner

LATERAL VENT STICK AIR FRESHENER

CROSS-REFERENCE TO RELATED APPLICATIONS

This patent application is a continuation of U.S. patent application Ser. No. 17/082,285, filed Oct. 28, 2020, which is a continuation of U.S. patent application Ser. No. 16/173,865, filed Oct. 29, 2018 and granted as U.S. Pat. No. 10,850,594, which is a continuation of U.S. patent application Ser. No. 15/255,537, filed Sep. 2, 2016 and granted as U.S. Pat. No. 10,232,683, which claims priority from U.S. Provisional Patent Application Ser. No. 62/247,544, filed Oct. 28, 2015, all of which are hereby incorporated herein by reference in their entirety.

The subject matter disclosed in this application is generally related to subject matter shown and described in U.S. Pat. Nos. 7,687,038; 7,687,037; 8,147,761; 8,480,960; D594,954; 8,460,609; D640,359; D650,892; 8,685,330; D689,181; and 9,155,812; which are hereby incorporated herein by reference.

BACKGROUND

The present disclosure relates generally to air fresheners. Various different types of air fresheners have been developed, particularly for use in vehicles. Vent stick type air fresheners include an aromatic body carried by the air vent, and utilizing air flow therefrom to disperse scent from the body.

SUMMARY

It has been recognized that it would be advantageous to develop an air freshener that can improve scent release and/or dispersal.

The disclosure provides an air freshener with a carrier having a pair of tabs defining a gap therebetween. A center tab extends from the pair of tabs and defines a front face of the carrier and defines a longitudinal axis along which the center tab extends from the pair of tabs. The pair of tabs extends laterally with respect to the longitudinal axis of the center tab in opposite directions. The pair of tabs has a lateral width greater than a longitudinal depth. At least one scented body is carried by one of the pair of tabs. The at least one scented body has a desired scent interspersed within a material of the body and diffusible out of the material of the body over time to provide the desired scent. The at least one scented body extends laterally with respect to the longitudinal axis of the scented tab in opposite directions. The at least one scented body has a lateral width greater than a longitudinal depth.

In addition, the disclosure provides an air freshener in combination with an air vent of a vehicle having louvers extending across an opening of the air vent and having a front facing into the vehicle and having a longitudinal axis oriented out of the air vent. The air freshener comprises a carrier with a pair of tabs extending into the air vent defining a gap therebetween with a louver of the air vent in the gap and between the pair of tabs. The carrier has a front face disposed outside of the air vent. The pair of tabs extend laterally with respect to the longitudinal axis of the air vent and along a width of the louver. The pair of tabs has a lateral width greater than a longitudinal depth into the air vent. A pair of scented bodies is each one carried by a different one of the pair of tabs, and disposed in the air vent and between the louvers. The pair of scented bodies has a desired scent interspersed within a material of the bodies and diffusible out of the material of the bodies over time to provide the desired scent. The pair of scented bodies extends laterally with respect to the longitudinal axis of the air vent and along the width of the louver. The pair of scented bodies has a lateral width greater than a longitudinal depth into the air vent.

BRIEF DESCRIPTION OF THE DRAWINGS

Additional features and advantages of the disclosure will be apparent from the detailed description which follows, taken in conjunction with the accompanying drawings, which together illustrate, by way of example, features of the disclosure; and, wherein.

Figure 1:
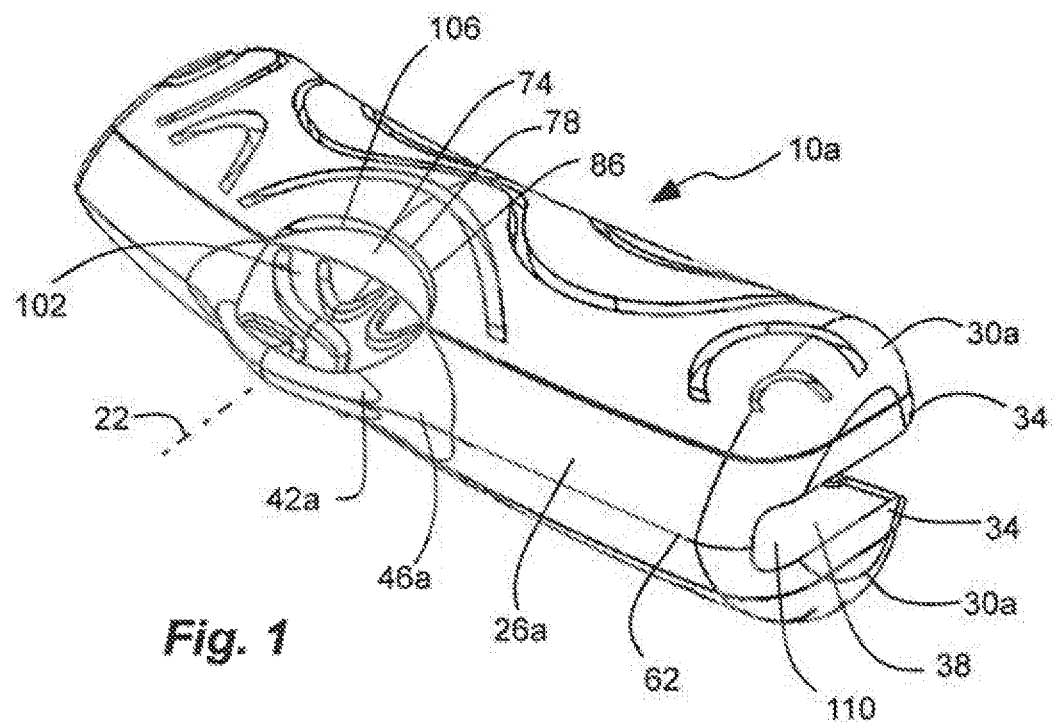
FIG. 1 is a front perspective view of an air freshener in accordance with an embodiment of the present disclosure.
Figure 2:
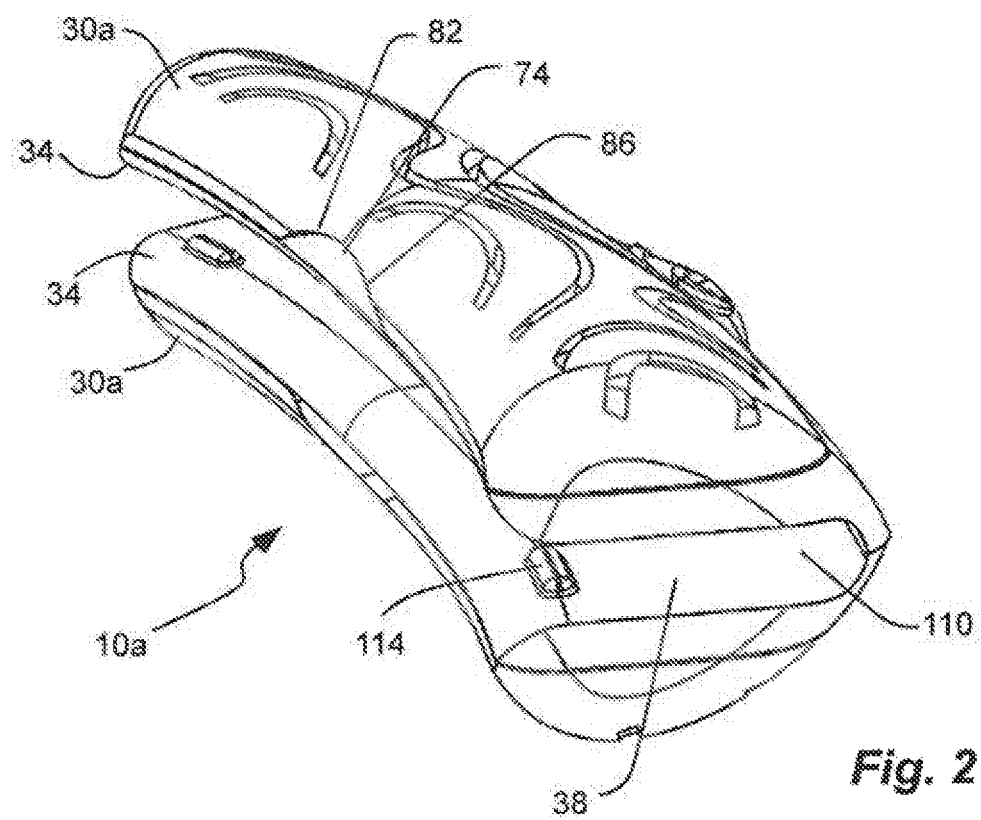
FIG. 2 is a rear perspective view of the air freshener of FIG. 1.

Reference will now be made to the exemplary embodiments illustrated, and specific language will be used herein to describe the same. It will nevertheless be understood that no limitation of the scope of the disclosure is thereby intended.

DETAILED DESCRIPTION OF EXAMPLE EMBODIMENT(S)

Definitions

The terms "vent" and "air vent" are used interchangeably herein to refer to an air outlet in a vehicle dashboard or console. The air outlet can be connected by ducts to a fan or blower to displace air through the duct to the air outlet. The air outlet can have a grid of louvers therein to further direct the airflow.

The terms "top" and "bottom" and "downwardly" and "upwardly" and the like are used herein relative to the air freshener device or housing thereof being oriented upright or vertical; while it is understood that the device or housing can be oriented horizontally or at an incline during use depending on the orientation of the power outlet.

The term "scent material" and "fragrant material" are used interchangeably herein to refer broadly to a material that carries a desired fragrance or scent, or even a neutralizing agent.

DESCRIPTION

The disclosure provides an air freshener for providing a desirable scent or fragrance. The air freshener can be used in an air vent of a vehicle. The air freshener can be passive, and can rely on diffusion of the scent, or the air displacement of the air through the vent in the vehicle. The air freshener can orient scent bodies laterally across the vent, as opposed to into the vent, to maximize air flow past the scent bodies and into the vehicle. In addition, the air freshener can have scent bodies that are laterally longer than their depth to accommodate shallow air vents.

Referring to FIGS. 1-10, air fresheners 10a and 10b are shown. The air fresheners can be used in combination with an air vent 14 (FIGS. 3 and 8) of a vehicle having louvers 18 (FIGS. 3 and 8) extending across an opening of the air vent, and having a front facing into the vehicle, and having a longitudinal axis 22 (extending out of the page in FIGS. 3 and 8) oriented out of the air vent, and perpendicular to an opening of the air vent. Air vents and louvers can have different sizes and configurations, as well as different depths.

The air fresheners 10a and 10b have a carrier 26a or 26b to carry a pair of (or at least one) scented bodies 30a or 30b. The carrier can clip to one of the louvers of the air vent, and hold the scented bodies in the air stream or air flow from the air vent. In addition, the carrier can impart rigidity and/or support to scented bodies that may be flexible and/or pliable. Furthermore, the carrier can orient the scented bodies laterally with respect to the air vent or longitudinal axis, or across the air vent. Thus, the air freshener can maximize the air flow across the scented bodies, and accommodate shallower air vents.

Figure 4:
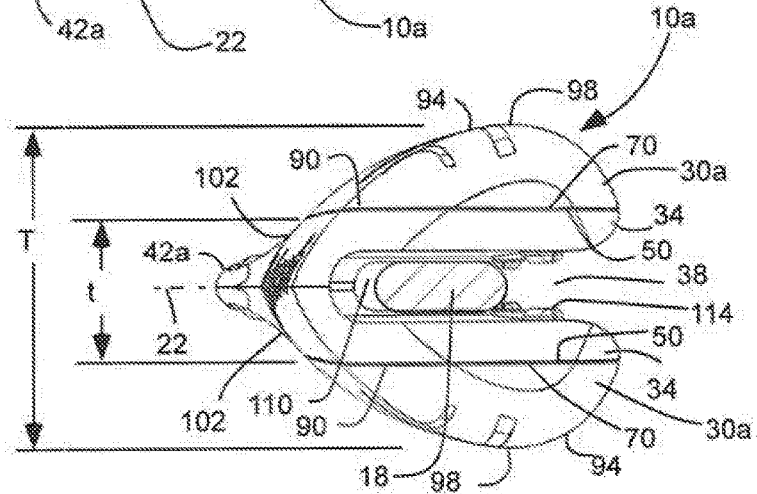
FIG. 4 is a side view of the air freshener of FIG. 1 shown with a louver of the air vent.
Figure 9:
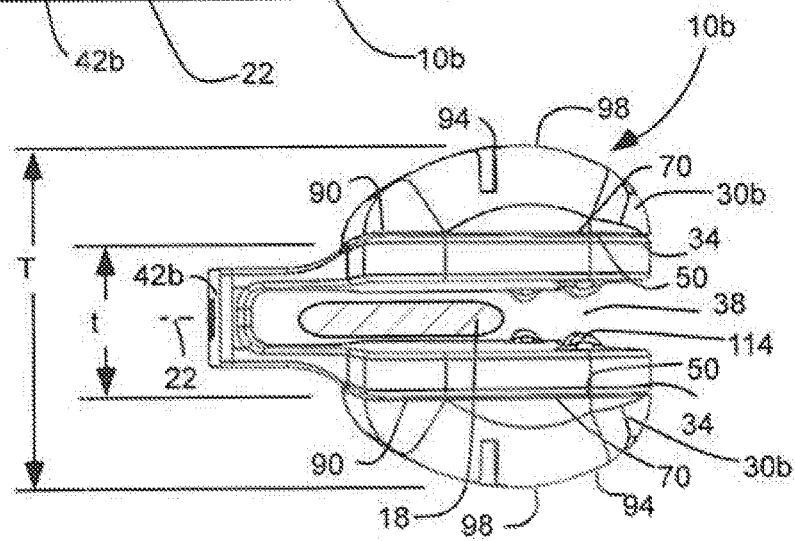
FIG. 9 is a side view of the air freshener of FIG. 6 shown with the louver of the air vent.

The carrier 26a or 26b has a pair of tabs 34 that are spaced-apart from one another, and that define a gap 38 therebetween. One tab can be an upper tab and the other tab can be a lower tab. In use, the tabs can extend into the air vent with a louver 18 of the air vent in the gap and between the pair of tabs, as shown in FIGS. 4 and 9. In addition, the carrier has a center tab 42a or 42b extending from the pair of tabs 34. In one aspect, the center tab can be disposed substantially between the tabs, or between planes defined by the tabs, or can extend from the gap between the tabs. The carrier has, and the center tab defines, a front face 46a or 46b of the carrier. The front face of the carrier is disposed outside the air vent, and faces out from the air vent and into the vehicle, and is thus visible is use. In one aspect, the front face 46a or 46b can include indicia 48, such as a logo, disposed so that it is visible in the vehicle. In addition, the center tab 42a or 42b can also define the longitudinal axis 22 along which the center tab extends from the pair of tabs. (The longitudinal axis of the air vent and the longitudinal axis of the carrier can correspond, or be parallel or coaxial in use.)

Figure 5:
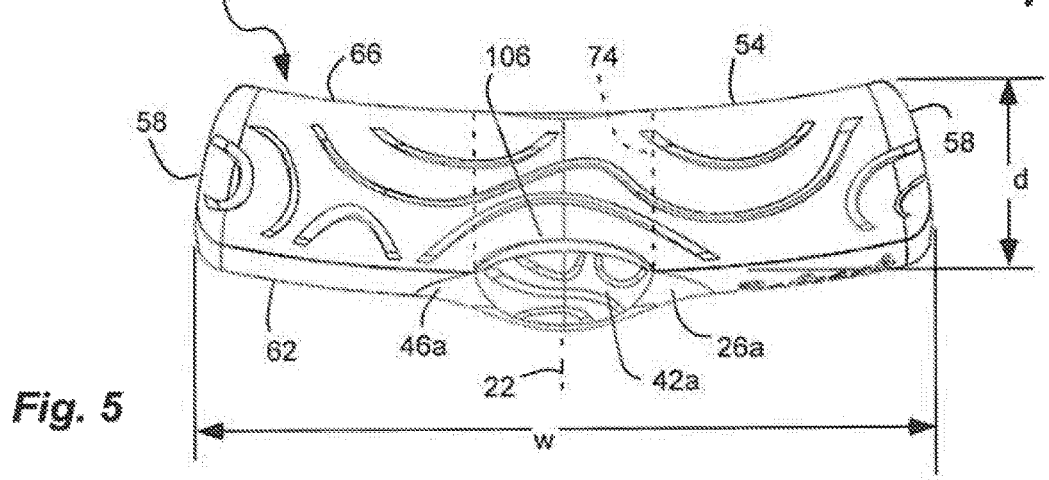
FIG. 5 is a top view of the air freshener of FIG. 1.
Figure 6:
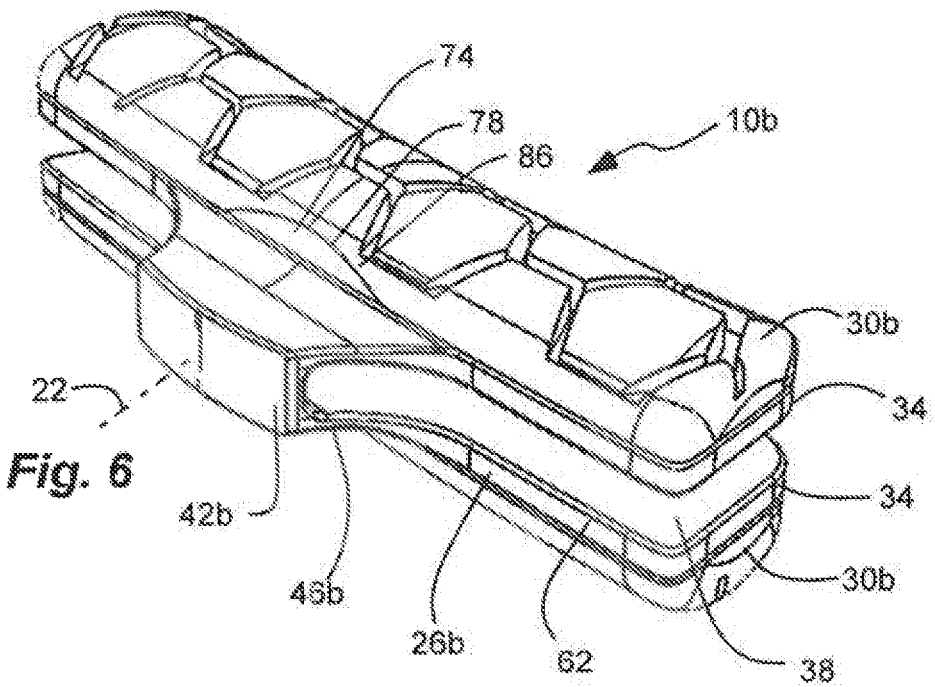
FIG. 6 is a front perspective view of another air freshener in accordance with another embodiment of the present disclosure.
Figure 7:
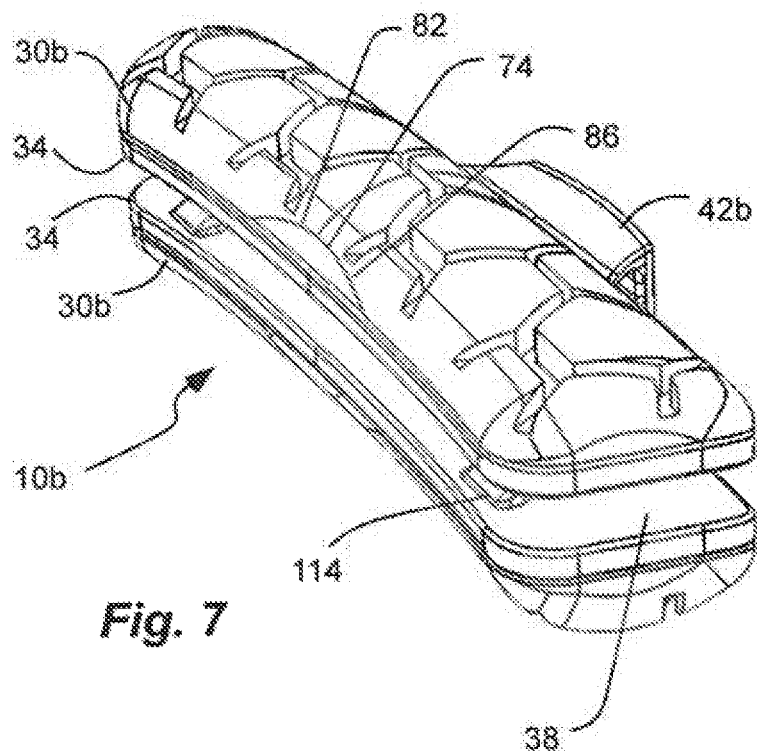
FIG. 7 is a rear perspective view of the air freshener of FIG. 6.
Figure 10:
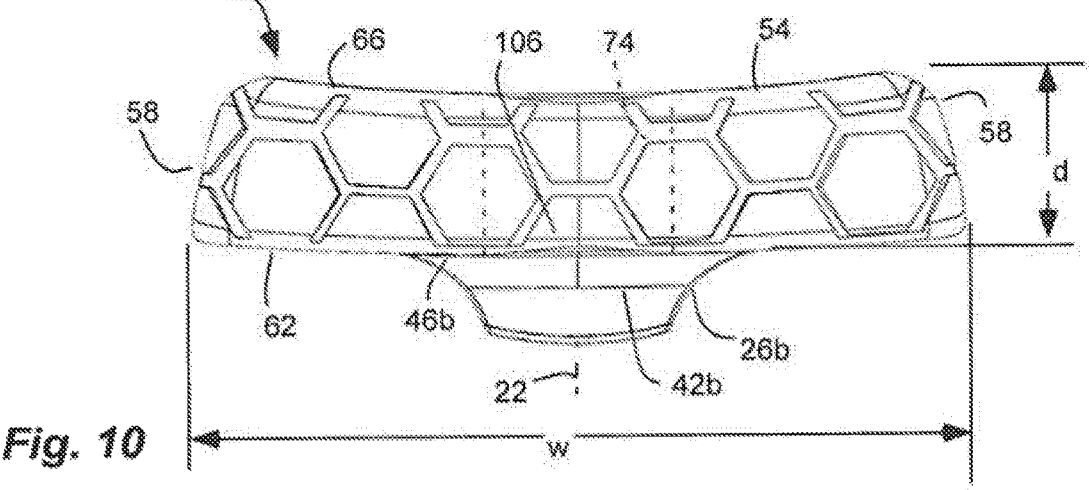
FIG. 10 is a top view of the air freshener of FIG. 6.

The pair of tabs 34 extend laterally with respect to the longitudinal axis 22 of the air vent or the center tab, in opposite directions (or on each side of the center tab) and along a width of the louver. The width of the louver is taken across the air vent or across an opening in the air vent, and perpendicular to the longitudinal axis. The pair of tabs 34 have a lateral width w greater than a longitudinal depth d into the air vent or along the longitudinal axis, as shown in FIGS. 5 and 10. Thus, as described above, the carrier and the tabs are configured to orient the scented bodies laterally.

The pair of tabs 34 have outward facing surfaces 50 (FIGS. 4 and 9) facing opposite directions from one another. One outward facing surface can face upwardly and the other outwardly facing surface can face downwardly. The outward facing surfaces can receive the scented bodies thereon. In addition, pins with enlarged heads can extend from the outward facing surfaces to secure the scented bodies to the tabs. The tabs 34 (and/or the scented bodies) can be arcuate and can extending in a broad arc, as shown in FIGS. 5 and 10, that is in a plane parallel with the louver. Thus, the front face 46a or 46b of the carrier 26a or 26b can be convex can be oriented to face longitudinally out of the air vent. In addition, the carrier 26a or 26b can have a concave back 54 (FIGS. 5 and 10) oriented to face longitudinally into the air vent. The arcuate shape of the tabs and the concave back of the carrier can present a concave leading edge of the carrier to facilitate installation on the louver. In addition, the arcuate shape of the tabs and the convex front face can reduce sharp edges extending into the vehicle to avoid inadvertent snagging.

In addition, the pair of tabs 34 (and/or the scented bodies) and/or the carrier 26a or 26b can have lateral ends 58 (FIGS. 5 and 10) that are tapered. The pair of tabs 34 (and/or the scented bodies) and/or the carrier 26a or 26b can have forward ends 62 (or the front face 46a or 46b) that can be wider than rearward ends 66 (or the back 54) of the pair of tabs, the carrier and/or the pair of scented bodies. The tapered lateral ends 58 can facilitate dispersal of the air flow by directing air outwardly.

The carrier can be formed of plastic, and can be formed by injection molding. The pair of tabs 34 can be formed integrally with and at the same time as the center tab 42a or 42b.

Figure 3:
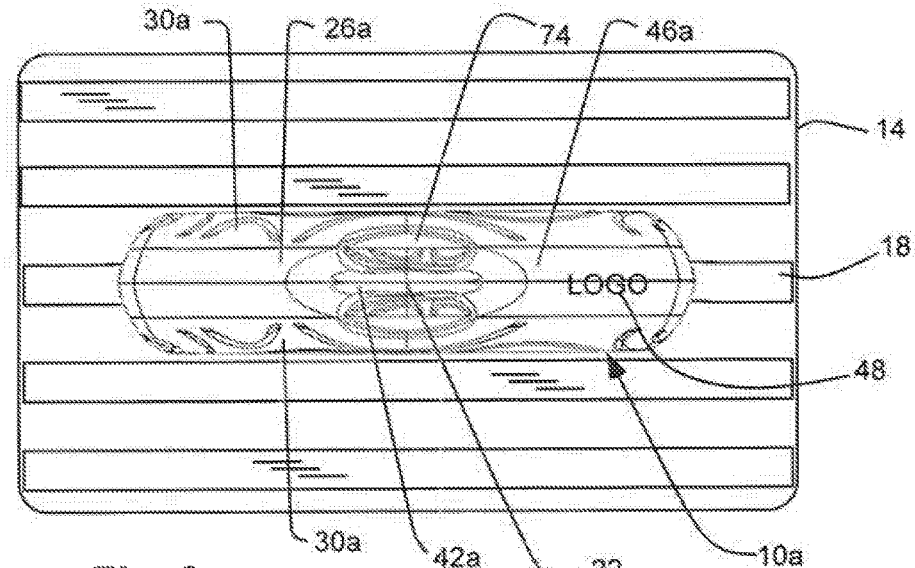
FIG. 3 is a front view of the air freshener of FIG. 1 shown in an air vent of a vehicle.
Figure 8:
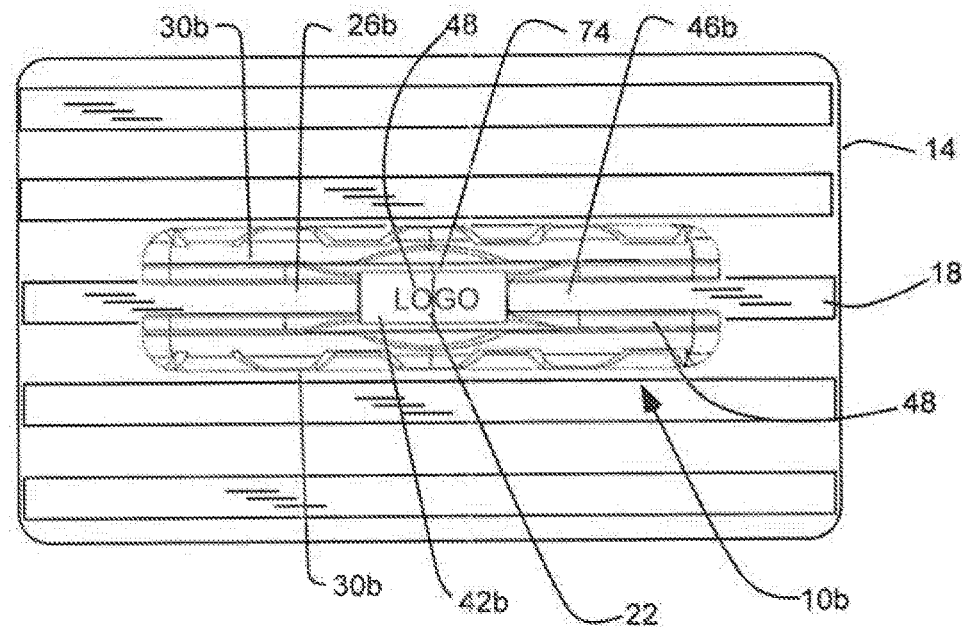
FIG. 8 is a front view of the air freshener of FIG. 6 shown in the air vent of the vehicle.

The scented bodies 30a or 30b are each carried by a different one of the tabs 34. In one aspect, a pair of scented bodies are carried by a pair of tabs, as shown. In another aspect, a single, or at least one, scented body is carried by one of the tabs. In use, the scented bodies are disposed in the air vent 14, and between the louvers 18, as shown in FIGS. 3 and 8. The scented bodies 30a or 30b have a desired scent interspersed within a material of the bodies, and diffusible out of the material of the bodies over time to provide the desired scent. In one aspect, the scent bodies can be formed of a polymer material, with a scent material, different than the polymer material, and with a different scent than the polymer material, interspersed with the polymer material. The scent body can have one or more indentations or grooves (or protrusions) formed therein to increase the exposed surface area of the scent body to maximize scent dispersal from the polymer material.

As described above, the pair of scented bodies 30a or 30b extend laterally with respect to the longitudinal axis 22 of the air vent or the center tab, and along the width of the louver. The pair of scented bodies 30a or 30b have a lateral width w greater than a longitudinal depth d into the air vent or along the longitudinal axis, as shown in FIGS. 5 and 10. Thus, as described above, the scented bodies are oriented laterally to increase the amount of air flowing over the bodies and into the vehicle. In one aspect, the lateral width of the pair of scented bodies extends substantially the lateral width of the pair of tabs, or they both have the same width. Thus, an entire width of the bodies is supported by the carrier and/or tabs. The pair of scented bodies 30a and 30b can have inward facing surfaces 70 (FIGS. 4 and 9) facing towards one another, and towards the outward facing surfaces 50 of the pair of tabs 34. One inward facing surface can face upwardly (towards the downwardly facing surface of the corresponding tab), while the other inward facing surface can face downwardly (towardly the upwardly facing surface of the corresponding tab). The inward facing surfaces 70 can abut to the outward facing surfaces 50. Indentations or bores can be formed in the inward facing surfaces to receive the pins to secure the scented bodies to the tabs. In one aspect, the scented bodies can be removably secured so the tabs so that they can be removed and replaced.

Furthermore, the air freshener 10a or 10b can have an air tunnel extending therethrough and aligned with the longitudinal axis. In one aspect, one or more air flow passages 74 can be formed between an adjacent tab 34 and scented body 30a or 30b. The air flow passage 74 can have a forward opening 78 in the front of the air freshener, and a rearward opening 82 in a rear of the air freshener. Thus, air flow can pass through the air freshener, as well as over or around the air freshener. And air can flow around more of the scented bodies, such as the inward facing surfaces 70. In one aspect, a pair of slots 86 can each be formed in a different one of the inward facing surfaces of the pair of scented bodies, and oriented longitudinally, to define the air flow passage.

The carrier 26a or 26b can have a thickness t between outermost surfaces 90 (FIGS. 4 and 9) or the outward facing surfaces 50 of the pair of tabs 34. Thus, the outward facing surfaces 50 can be outermost surfaces of the carrier in a direction perpendicular to the lateral width of the pair of tabs. The thickness t of the carrier can be less than a thickness T defined between outermost surfaces 94 (FIGS. 4 and 9) of the pair of scented bodies 30a or 30b taken perpendicular to the lateral width of the pair of scented bodies. Thus, the carrier and/or the tabs do not interfere with air flow around the scented bodies, and the exposed surface area of the scented bodies is maximized. The scent bodies can extend above, and/or below, the pair of tabs to contact the air flow.

As described above, the scented bodies 30a or 30b can have lateral ends 58 (FIGS. 5 and 10) that are tapered. The scented bodies 30 or 30b can have forward ends 62 that can be wider than rearward ends 66 (or the back 54) of the scented bodies. The tapered lateral ends 58 can facilitate dispersal of the air flow by directing air outwardly.

In addition, an outermost exterior surface 98 of each of the pair of scented bodies 30a or 30b can have an arcuate profile taken along the longitudinal axis and perpendicular to the lateral width of the pair of scented bodies, as shown in FIGS. 4 and 9. The scent bodies, and the tabs, can have an arcuate profile to provide an aerodynamic flow of air around the scent bodies. In addition, the indentations or grooves (or protrusions) in the scent body can create a turbulent flow around the scent bodies to facilitate scent dispersal.

In one aspect, the center tab 42a can be defined between a pair of indentations 102 formed in each of the pair of tabs 34. Similarly, each of the pair of scented bodies 30a can have an indentation 106 corresponding to a respective indentation 102 in a corresponding tab. The indentations 102 and 106 can facilitate grasping the center tab 42a to place and remove the air freshener from the vent.

In one aspect, the carrier 26a can be configured with the front face 46a extending substantially the entire lateral width of the carrier, and the tabs 34, as shown in FIGS. 1-5. Thus, the front face can extend substantially the entire lateral width of the gap 38 to cover the gap at the front face. The pair of tabs 34 and the front face 46a can define a channel 110 to receive the louver therein 18. The front face 46a and the channel 110 can help stabilize the carrier 26a on the louver.

In another aspect, the carrier 26b can be configured with the front face 46b extending partially along the lateral width of the carrier, and partially along the tabs 34, as shown in FIGS. 6-10. Thus, a front of the gap 38 is exposed to expose the gap. The open gap can accommodate increased air flow.

Furthermore, the carrier 26a or 26b, or the tabs 34, can have nobs or teeth 114 extending from the tabs and into the gap 38 and/or channel 110 to help grip the louver 18.

The indicia can include a logo of a business or company. The terms "business" and "company" are used broadly and interchangeably herein to refer to an organization that provides a product or a service. The business, company or organization can have a name, logo, slogan, trademark, service mark, etc. that is capable of identifying and/or distinguishing the business or company, or product or service, or both, or can otherwise be utilized to market, promote, and/or brand the business or company, or product or service, or both. In addition, the indicia can include instructions for use, or warnings.

While the forgoing examples are illustrative of the principles of the present disclosure in one or more particular applications, it will be apparent to those of ordinary skill in the art that numerous modifications in form, usage and details of implementation can be made without the exercise of inventive faculty, and without departing from the principles and concepts of the disclosure. Accordingly, it is not intended that the disclosure be limited, except as by the claims set forth below.

The invention claimed is:

1. An air freshener comprising:
   a carrier configured for insertion into an air vent along a longitudinal insertion axis of the carrier, the carrier comprising:
   a front face oriented to face out of the air vent when the carrier is received within the air vent;
   a back side opposite the front face and oriented to face into the air vent when the carrier is received within the air vent, the carrier having a longitudinal depth defined between the front face and the back side;
   a first lateral end and an opposed second lateral end each extending longitudinally from the front face to the back side, the carrier having a lateral width defined between the first lateral end and the second lateral end, wherein the lateral width of the carrier is greater than the longitudinal depth; and
   a first tab and a second tab extending longitudinally from the front face to the back side, the first tab and the second tab each having an inward facing surface and an opposed outward facing surface, the inward facing surfaces of the first tab and the second tab defining a gap therebetween; and
   a scented body including a material having a scent interspersed therein and diffusible out of the material to disperse the scent, the scented body secured to the outward facing surface of at least one of the first tab and the second tab.

2. The air freshener of claim 1, wherein the scented body extends continuously across the longitudinal depth of the carrier between the front face and the back side, the scented body further extending continuously across the lateral width of the carrier between the first lateral end and the second lateral end.

3. The air freshener of claim 2, wherein the scented body has a lateral width that is greater than a longitudinal depth of the scented body.

4. The air freshener of claim 1, wherein the scented body includes an inner surface and an opposed outer surface, the inner surface facing the outward facing surface of the at least one of the first tab and the second tab, and wherein the scented body defines a plurality of indentations recessed on the inner surface.

5. The air freshener of claim 4, wherein the inner surface of the scented body contacts the outward facing surface of the at least one of the first tab and the second tab, and wherein the indentations are spaced from the outward facing surface.

6. The air freshener of claim 4, wherein the scented body further defines a plurality of indentations recessed on the outer surface.

7. The air freshener of claim 4, wherein the outer surface of the scented body is curved to define an arcuate profile along the longitudinal insertion axis between the front face and the back side.

8. The air freshener of claim 1, wherein the front face has a concave curvature.

9. The air freshener of claim 8, wherein the front face extends the entire lateral width of the carrier from the first lateral end to the second lateral end.

10. The air freshener of claim 1, wherein the gap is sized to receive a louvre of the air vent therein.

11. The air freshener of claim 1, wherein the carrier is formed of an injection molded plastic.

12. A carrier for an air freshener, the carrier comprising:
a front face;
a back side opposite the front face, the front face and the back side defining a longitudinal insertion axis of the carrier extending therebetween, the carrier configured for insertion into an air vent along the longitudinal insertion axis such that, when the carrier is received within the air vent, the front face is oriented to face out of the air vent and the back side is oriented to face into the air vent;
a first lateral end and an opposed second lateral end each extending longitudinally from the front face to the back side, the carrier having a lateral width defined between the first lateral end and the second lateral end and a longitudinal depth defined between the front face and the back side, wherein the lateral width of the carrier is greater than the longitudinal depth; and
a first tab and a second tab extending longitudinally from the front face to the back side, the first tab and the second tab each having an inward facing surface and an opposed outward facing surface, the inward facing surfaces of the first tab and the second tab defining a gap therebetween, the outward facing surface of the first tab and the second tab each being adapted to secure a scented body of the air freshener thereon.

13. The carrier of claim 12, wherein the front face has a concave curvature.

14. The carrier of claim 13, wherein the front face extends the entire lateral width of the carrier from the first lateral end to the second lateral end.

15. The carrier of claim 12, wherein the gap is sized to receive a louvre of the air vent therein.

16. The carrier of claim 12, wherein the carrier is formed of an injection molded plastic.

17. The carrier of claim 12, wherein the first lateral end and the second lateral end are tapered to direct air flow around the carrier.

18. An air freshener comprising:
a carrier configured for insertion into an air vent along a longitudinal insertion axis of the carrier, the carrier comprising:
a first longitudinal end oriented to face out of the air vent when the carrier is received within the air vent;
a second longitudinal end opposite the first longitudinal end and oriented to face into the air vent when the carrier is received within the air vent, the carrier having a longitudinal depth defined between the first longitudinal end and the second longitudinal end;
a first lateral end and an opposed second lateral end each extending longitudinally from the first longitudinal end to the second longitudinal end, the carrier having a lateral width defined between the first lateral end and the second lateral end, wherein the lateral width of the carrier is greater than the longitudinal depth;
a first tab and a second tab extending longitudinally from the first longitudinal end to the second longitudinal end, the first tab and the second tab each having an inward facing surface and an opposed outward facing surface, the inward facing surfaces of the first tab and the second tab defining a gap in the second longitudinal end sized to receive a louvre of the air vent therein; and
at least one scented body secured to the carrier and positioned to extend longitudinally from the first longitudinal end to the second longitudinal end, the at least one scented body including a material having a scent interspersed therein and diffusible out of the material to disperse the scent.

19. The air freshener of claim 18, wherein the at least one scented body includes an inner surface oriented to face the carrier and an opposed outer surface, and wherein the at least one scented body defines a plurality of indentations recessed on the inner surface.

20. The air freshener of claim 19, wherein the outer surface of the at least one scented body is curved to define an arcuate profile along the longitudinal insertion axis between the first longitudinal end and the second longitudinal end.

* * * * *